(12) United States Patent
Yamanouchi

(10) Patent No.: US 6,632,229 B1
(45) Date of Patent: Oct. 14, 2003

(54) ORGAN ANASTOMOSING APPARATUS AND METHOD

(75) Inventor: Eigoro Yamanouchi, Misato (JP)

(73) Assignee: Yugengaisha Pacs Optica Japan, Misato (JP)

( * ) Notice: Subject to any disclaimer, the term of this patent is extended or adjusted under 35 U.S.C. 154(b) by 458 days.

(21) Appl. No.: 09/640,761

(22) Filed: Aug. 18, 2000

(30) Foreign Application Priority Data

Aug. 19, 1999 (JP) .......................................... P11-232876
Mar. 15, 2000 (JP) ....................................... P2000-072550

(51) Int. Cl.⁷ .............................................. A61B 17/08
(52) U.S. Cl. ..................... 606/153; 606/159; 606/170; 606/180
(58) Field of Search ............................ 600/12, 15, 29, 600/30, 32; 604/48, 54, 49; 606/159, 151, 153, 155, 156, 170, 180; 128/898

(56) References Cited

U.S. PATENT DOCUMENTS

| | | | | |
|---|---|---|---|---|
| RE32,947 E | * | 6/1989 | Dormer et al. | 128/420.6 |
| 4,899,744 A | * | 2/1990 | Fujitsuka et al. | 606/153 |
| 5,595,562 A | | 1/1997 | Grier | |
| 5,690,656 A | * | 11/1997 | Cope et al. | 606/153 |
| 5,702,412 A | * | 12/1997 | Popov et al. | 606/159 |
| 6,068,637 A | * | 5/2000 | Popov et al. | 606/159 |

FOREIGN PATENT DOCUMENTS

| | | |
|---|---|---|
| EP | 0 754 434 | 1/1997 |
| WO | WO 81/00668 | 3/1981 |
| WO | WO 97/12555 | 4/1997 |

* cited by examiner

*Primary Examiner*—John J. Calvert
*Assistant Examiner*—Robert H. Muromoto, Jr.
(74) *Attorney, Agent, or Firm*—Oblon, Spivak, McClelland, Maier & Neustadt, P.C.

(57) ABSTRACT

An apparatus for anastomosing an organ of a subject to be anastomosed such as patient comprises a pair of magnets being disposed to predetermined sites or regions of organs of the subject each other so as to be opposed through wall portions of the respective organs, the magnets being adsorbed to each other so as to form an anastomosis site having a through hole for making communication between the organ walls, a flexible soft guide wire detachably mounted to at least one of the paired magnets, and a guide tube inserted into a body of the subject with the guide wire being inserted therein, the guide tube coming into contact with a guide wire mount surface of the one of magnets so as to support the one magnet when the guide wire is removed from the one magnet and the guide tube being inserted into the through hole of the anastomosis site to maintain formation of the through hole.

24 Claims, 9 Drawing Sheets

ORGAN ANASTOMOSING APPARATUS AND METHOD

BACKGROUND OF THE INVENTION

1. Technical Field of the Invention

The present invention relates to an organ anastomosing apparatus and method for forming a bypass by strongly pinching and pressing walls of the adjacent organs of a subject such as patient by adsorbing a pair of magnets to each other so as to cause apoptosis to locally occur and forming a through hole (a passage) for making communication between the organs and anastomosis region around the through hole.

2. Prior Art

In general, the anastomosis of organs such as gut of a body of a subject (which may be described as subject's body hereinlater) is frequently performed to form a bypass (a through hole) between two cavity guts, for example, in order to flow the content of the gut or bile of bile duct again when constriction of the gut or bile duct progresses by its tumor, ulcer, inflammation, or trauma and the like.

An example of a conventional organ anastomosing apparatus used for such type of the anastomosis is described in Japanese Patent Laid-open Publication No. HEI 9-10218. In this example, a pair of magnets capable of being automatically self-centered are disposed on both sides of two organ walls to be anastomosed. By adsorption of a pair of the large and small magnets, the organ walls are strongly pinched from both sides and are compressed (pressed to be pinched) to cause apoptosis to locally occur, thereby forming the anastomosis with the through hole (fistula) and the peripheral rim (edge) of a small magnet is formed at a sharp cut rim (edge) for promoting the anastomosis.

However, in such conventional organ anastomosing apparatus, the peripheral rim of a small magnet is formed at a sharp cut rim. Thus, there is a fear that the other many organs mare damaged by the cut rim until this small magnet is inserted into a predetermined organ, is inducted into a predetermined site (region), and is disposed at the site.

In addition, after the anastomosis with the through hole has been formed by the adsorption of a pair of magnets, there is no means for holding the through hole formation. Thus, after the anastomosis, for example, it is required to take complicated steps, such that a drainage tube is inserted into the body independent of the organ anastomosing apparatus and inducted to the through hole to be inserted into the through hole, and that the inserted state must be maintained about three months until the anastomosis has been completed.

Further, an N-pole face and an S-pole face on the adsorption surfaces of a pair of magnets each have only one face. Thus, if the adsorption surfaces are disposed in opposite to each other with high precision via an organ wall of the subject, the same poles resist against each other and cannot be adsorbed by each other so that it is required for these magnets to have high disposition precision, and a pair of magnets are not always adsorbed easily.

SUMMARY OF THE INVENTION

The present invention was conceived to overcome or solve the defects or problems encountered in the prior art mentioned above and to provide an organ anastomosing apparatus and method capable of safely disposing a pair of magnets at predetermined sites or regions each in one of organs without almost damaging the other organ and forming anastomosis and capable of simply and reliably achieving through hole formation after the anastomosis.

It is another object of the present invention to provide an organ anastomosing apparatus and method capable of simply and reliably performing alignment between the adsorption surfaces of a pair of magnets at predetermined regions in the organs of a subject to be anastomosed.

These and other objects can be achieved according to the present invention by providing, in one aspect, an organ anastomosing apparatus comprising:

a pair of magnets being disposed to predetermined sites of organs of a subject to be anastomosed to each other so as to be opposed to each other through wall portions of the respective organs, the magnets being mutually adsorbed to each other so as to form an anastomosis site having a through hole for making communication between the organ walls;

a flexible guide wire detachably mounted to at least one of the paired magnets; and a guide tube inserted into a body of the subject with the guide wire being inserted therein, the guide tube coming into contact with a guide wire mount surface of the one of magnets so as to support the one magnet when the guide wire is removed from the one magnet, the guide tube being inserted into the through hole of the anastomosis site to maintain formation of the through hole.

In preferred embodiments of this aspect, the apparatus further comprises a cylindrical sheath inserted into the body of the subject from an outside thereof so as to insert the one magnet to which the guide wire is mounted to guide the one magnet in a vicinity of the predetermined sites of organs.

The one magnet has an adsorption surface larger than that of the other one magnet. The paired magnets may be formed in substantially a same size. A surface of the magnet is coated with at least one of an acid resistant membrane and a thrombus resistant membrane. The magnet may be formed of a rare earth element.

The other one magnet is taken into the subject's body and then guided from an outside thereof by means of an induction magnet to a predetermined site of the organ of the subject. The induction magnet has an N-pole and an S-pole opposite to each other and an axial intermediate portion to which a stem is provided so as to extend in a direction perpendicular to the axial intermediate portion.

The other one magnet is removably pinched by pinching means of an endoscope to be disposed at the predetermined site of the organ of the subject's body. The pinching means of the endoscope is made of a non-magnetic material. The other one magnet is provided with a flexible non-magnetic holding member to be pinched by the pinching means of the endoscope.

The organ may be one of digestive system, blood vessel, ureter, bladder, skin and bone.

According to the present invention, when a pair of magnets disposed in opposite to each other via each organ wall of the subject's body are adsorbed to each other, the organ wall is pinched from both sides by a pair of the magnets and is compressed (pressed to be pinched). Then, the apoptosis occurs and the through hole making communication between the organ walls is formed. At the same time, the peripheral rim of the through hole adheres, the anastomosis is formed and a bypass is thereby formed. Then, a guide tube and a guide wire are removed from one magnet. Further, a tip end of the guide tube is inserted into the through hole of the anastomosis site and the inserted state is maintained until the anastomosis has been completed. In this manner, the formation of the through hole at the anastomosis site is maintained. On the other hand, a pair of magnets removed, with being adsorbed to each other, are discharged to the outside of the body together with the dejection.

Therefore, according to the present invention, unlike the prior art, since the peripheral rim of the magnet is not formed at a sharp cut rim. There can be effectively prevented such a fear that the other many organs are damaged by the cut rim until the magnet is inserted into a predetermined organ, is inducted into a predetermined site, and is disposed at the site.

In addition, after the anastomosis with the through hole has been formed on the organ walls by the adsorption of a pair of magnets to thereby form the through hole, the guide tube already inserted into the subject's body in the vicinity of the anastomosis site together with one magnet is inserted into the through hole of the anastomosis site immediately, and the inserted state is maintained until the anastomosis has been completed. In this manner, the formation of the through hole can be easily maintained. Therefore, unlike the prior art, after the anastomosis, there can be eliminated the complicated steps, such that a drainage tube is inserted into the body independent of the organ anastomosing apparatus and is inducted to the through hole to be inserted into the through hole and that the inserted state must be maintained about three months until anastomosis has been completed.

Further, for example, there are provided a plurality of the adsorption surfaces of the other magnet taken by the subject's body, and thus, a pair of magnets are easily adsorbed to each other.

One magnet can be guided in the vicinity of a predetermined organ's site into the subject's body from the outside thereof by merely inserting the magnet into the sheath and the easiness and precision of the guiding can be improved.

According to the present invention, one magnet has an adsorption surface greater in size than the other magnet. Thus, the adsorption of one magnet to the other magnet at a predetermined site inside of the body can be easily and reliably performed and the operation time can be reduced. Therefore, the fatigue of the subject's body can be reduced.

In addition, the through hole of the anastomosis site is formed in substantially the same size as that of the adsorption surface of a smaller magnet. This makes it possible to prevent a larger magnet from moving to the organ side of the smaller magnet through the through hole.

According to the present invention, in the case of anastomosis in intestines between large and small intestines, magnets having substantially the same size and shape are used. After the anastomosis has been completed, the magnets are inducted so as to be moved to the large intestine while the magnets being adsorbed to each other, for example, and are discharged to the outside of the body together with dejection.

According to the present invention, the surface of the magnet is coated with an acid resistant membrane. This makes it possible to prevent degeneration or degradation due to oxidization with the acidic fluid inside of the body. In addition, the surface of the magnet is coated with a thrombus resistant membrane. This makes it possible to prevent generation of thrombus due to the magnets in blood.

According to the present invention, since the magnet is made of a rare earth element, a magnetic force can be strengthened. For this reason, even in the case where a thick organ wall is targeted for forming the anastomosis, the adsorption between the magnets can be easily and reliably performed and the operation time can be reduced.

In addition, a pair of magnets having strong magnetic forces are adsorbed to each other, and thus, there can be improved the apoptosis of the organ wall to be strongly pressed to be pinched by the magnets, the reliability of the formations of the through hole and the anastomosis of the periphery of the through hole.

According to the present invention, after the other magnet has been taken into the subject's body, the magnet can be guided from the outside of the body to the predetermined organ site by means of the induction magnet. Thus, a work for positioning the other magnet can be simplified and the positioning precision can be improved.

According to the present invention, the N-pole and S-pole are provided at both ends in the axial direction of the magnet main body. Thus, a stem of the magnet is turned around its central axis, whereby the magnetic pole of the magnet main body is properly adsorbed or resisted towards the magnet in the body and the magnet can be inducted to a predetermined site in the body.

According to the present invention, the other magnet is removably pinched by pinching means such as pinching forceps of an endoscope and is disposed at a predetermined site of an organ. Thus, the other magnet can be disposed at the predetermined organ site while observing the carrying state of the magnet in the body by the endoscope. For this reason, the positioning precision of the other magnet can be improved.

The pinching means such as pinching forceps of the endoscope is made of a non-magnetic material. This makes it possible to prevent a magnet from being hardly removed from the pinching means due to the adsorption of the magnet to the pinching means of the endoscope. Furthermore, the other magnet comprises a non-magnetic flexible soft pinching member to be pinched by the pinching means of an endoscope. Thus, the non-magnetic holding member of the other magnet can be easily and reliably pinched by the pinching means of the endoscope. Moreover, since the holding member of the other magnet is soft, the organs in the subject's body can be prevented from being damaged.

According to the present invention, the organ anastomosing apparatus according to any one of the first aspect to the eleventh aspect can be used to form the anastomosis of any organ including digestive system, blood vessel, ureter, bladder, skin, and bone.

In another aspect of the present invention, there is provided an organ anastomosing method comprising the steps of:

preparing a pair of magnets to at least one of which a flexible guide wire is detachably mounted, guide tube to be disposed to come into contact with a guide wire mount surface of the one magnet and a cylindrical sheath to guide the guide wire;

disposing one of a pair of magnets at a predetermined site of one of organ walls of a subject to be anastomosed to each other;

inserting the cylindrical sheath from an outside of a subject into a body of the subject;

inserting the other magnet for detachably mounting the flexible guide wire into the sheath and inserting the magnet into the other one of organ walls so as to dispose the magnet at a predetermined site, the organ being adsorbed by the one magnet to pinch a portion of the organ wall by a pair of the magnets;

forming a through hole for making communication between the organ walls by pinching the organ walls and forming an anastomosis around the through hole;

removing the guide wire from the other one magnet by pulling the guide wire towards the outside of a body of the subject at a time when the guide tube is inserted into the sheath so as to support a tip end of the guide tube in contact with a guide wire mount surface of the other one magnet;

leaving the guide tube for a predetermined period of time while inserting the guide tube into the through hole of the anastomosis site; and pulling out the guide tube from the anastomosis site and the subject's body after an elapse of a predetermined period of time.

In a preferred embodiment of this aspect, the one magnet is inducted from the outside of the body of the subject and guided to the predetermined site of the organ. The one magnet is removably pinched by pinching means of an endoscope and disposed at the predetermined site of the organ. One of the paired magnets has an adsorption surface larger in size than that of the other one magnet.

According to the present invention, after an anastomosis site at which the anastomosis with the through hole is formed on the organ wall due to the adsorption of a pair of magnets is formed, when a guide tube is inserted into the subject's body while a guide wire is inserted therein, and the guide wire is pulled towards the outside of the body while the wire is supported in contact with the guide wire mount surface of one magnet, the guide wire is removed from one magnet. Then, when the guide tube is inserted into the through hole of the anastomosis site, a pair of magnets adsorbed to each other are pushed out from the anastomosis site. Then, the guide tube is inserted into the through hole of the anastomosis site and is left in the subject's body until the anastomosis has been completed and stopped. In this manner, the formation of the through hole of the anastomosis site can be easily maintained. Therefore, as in the prior art, there can be eliminated the complicated steps, such that a drainage tube is inserted into the body independent of the organ anastomosing apparatus and is inducted to the through hole to be inserted into this through hole, and the inserted state must be maintained about three months until anastomosis has been completed and stopped.

According to the present invention, one magnet is inducted from the outside of the body by means of the induction magnet and is guided to a predetermined site of an organ. Thus, there is no need to take an endoscope by the subject's body and one magnet can be easily guided to the predetermined site of the subject's body.

According to the present invention, one magnet is removably pinched by pinching means such as pinching forceps of the endoscope and is disposed to a predetermined site of an organ. Thus, the magnet can be disposed at the predetermined site of the organ while observing the carrying state of the one magnet in the body by the endoscope. Therefore, the positioning precision of one magnet can be improved.

According to the present invention, one magnet has an adsorption surface greater than the other magnet. Thus, the adsorption to the other magnet at a predetermined site in the body can be easily and reliably performed, and the work time can be reduced. For this reason, the fatigue of the subject's body can be reduced.

In a further aspect, there is provided an organ anastomosing apparatus, which is characterized in that a pair of magnets are disposed in opposite to each other at a predetermined site of a subject's organs to be anastomosed each other via respective organ walls, the pair of magnets being adsorbed to each other so as to form an anastomosis site having a through hole making communication between the organ walls and that a large diameter end larger than those of the respective ends and through hole is provided at each end of an opposite side of both the adsorption surfaces of a pair of the magnets.

In this aspect, each magnet has a grip provided on an outer end surface of the large diameter end. The large diameter end of each magnet is made of a row material fusible in the subject's body after an elapse of a predetermined period of time.

At least one of a pair of magnets is mounted with a spacer made of a non-magnetic material at the other end thereof.

The organ anastomosing apparatus may further comprise a drainage tube to be inserted into the subject's body, the drainage tube guiding movement of one of a pair of magnets along an outer surface thereof and a sign indicative of the moving direction of the magnet is marked with a radiation transmission-free material.

A substance promoting anastomosis of membrane growth factors in blood vessels or the like is adhered to the magnets or the spacer mentioned above.

According to the present invention, when a pair of magnets disposed in opposite to each other via the organ wall of the subject's body are adsorbed to each other, the organ wall is pinched by a pair of the magnets from both sides thereof and strongly compressed (pressed to be pinched). Then, the apoptosis occurs, the through hole is formed and the peripheral rim of the through hole adheres, whereby the anastomosis is formed and a bypass is formed. At this time, although a pair of the magnets adsorbed to each other are still inserted into the though hole (bypass), the large diameter end of each of the magnets is greater than a diameter of the through hole. Thus, the end is fitted to the anastomosis site around the through hole and pulling-out is inhibited. Therefore, a pair of magnets adsorbed to each other are left in the state in which the magnets are inserted into the through hole during a desired period of time (for example, about three months), whereby recurrent occlusion due to the progressing of the anastomotic adhesion of the through hole can be prevented.

After the recurrent occlusion has been prevented, one of a pair of magnets adsorbed to each other is pinched by a pinching forceps of the endoscope, for example, and a force for forcibly pulling out the magnet from the through hole is applied thereto, whereby the anastomosis site around the through hole is elastically deformed and the magnet can be pulled out from the through hole. In this manner, the formation of the through hole of the anastomosis site can be maintained.

According to the present invention, a grip is provided on the outer surface of the large diameter end of each magnet. Thus, this grip is pinched by the pinching forceps of the endoscope, for example, whereby the magnet can be moved to a desired site of the desired organ wall in the subject's body.

According to the present invention, after the through hole (bypass) has been formed between the desired organ walls, even if each magnet is not removed from the subject's body, when a predetermined period of time is elapsed, the large diameter end of each magnet fitted to the peripheral rim of the through hole is gradually fused, and thus, the fitting is released. For this reason, a pair of magnets are moved to one organ through the through hole of the anastomosis site and are discharged to the outside of the body together with the dejection or the like. Therefore, a work for removing a pair of magnets to the outside of the subject's body after the bypass formation can be eliminated, and the safety can be improved.

According to the present invention, the axial length (thickness) of the spacer made of a non-magnetic material, which is provided at one end of at least one of a pair of magnets, is properly selected, whereby the magnetic adsorption force of each magnet itself can be properly selected without controlling the adsorption force. Thus, the magnetic adsorption force of the magnet, i.e., organ wall compression force can be properly selected according to a variety of circumferences such as organs to be anastomosed or wall thickness.

According to the present invention, one of a pair of magnets is moved along the outer surface of a drainage tube inserted into the subject's body, whereby the movement of the magnet can be guided to a desired organ or site by means of a drainage tube.

Moreover, when the magnet is moved while observing the the moving state through radiation transmission, a sign such as arrow marked on the outer surface of the drainage tube by the radiation transmission free material is visually checked, whereby the movement direction is checked. Thus, an erroneous directional movement of the magnet can be prevented, and the efficiency of magnet movement can be improved.

According to the present invention, after the through hole (bypass) has been punched on the desired organ wall by means of a pair of magnets, the anastomosis is promoted in contact with the anastomosis promoter such as membrane growth factors in blood vessels in which the opening peripheral rim of the through hole adheres to the magnets or the spacer.

It is to be noted that the nature and further characteristic features of the present invention will be made more clear from the following descriptions made with reference to the accompanying drawings.

DESCRIPTION OF THE PREFERRED EMBODIMENTS

Figure 1:
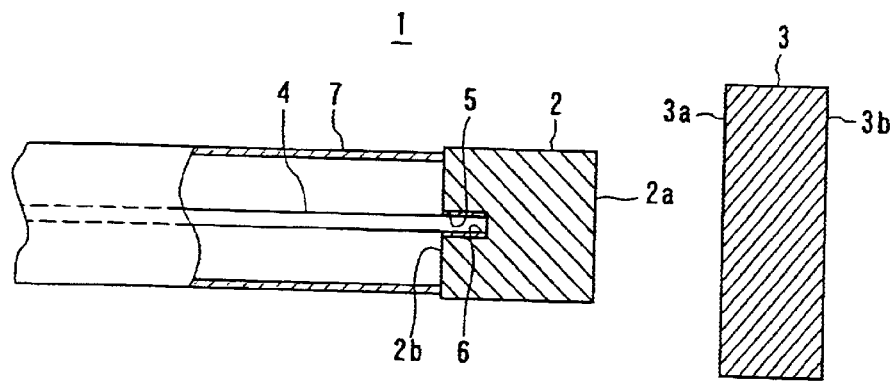
FIG. 1 is a partial longitudinal sectional view showing an organ anastomosing apparatus according to a first embodiment of the present invention.

Hereinafter, embodiments of the present invention will be described with reference to FIG. 1 to FIG. 8. In these figures, same or corresponding elements are designated by same reference numerals.

FIG. 1 is a partial longitudinal sectional view showing a structure of an organ anastomosing apparatus 1 according to a first embodiment of the present invention. This organ anastomosing apparatus 1 comprises a cylindrical magnet 2 having an adsorption surface 2a and having corner parts chamfered therefrom and a second flat cylindrical magnet 3 having an adsorption surface 3a which is greater in size than the adsorption surface 2a of the first magnet 2 and which is magnetically adsorbed to each other with different magnetic poles, the second flat cylindrical magnet 3 also having corner parts chamfered therefrom. The second magnet 3 is formed with an adsorption surface 3b on the back surface of the adsorption surface 3a whose magnetic poles are different from the of the adsorption surface 3a. These first and second magnets 2 and 3 each are made of a rare earth element, and the outer surfaces thereof are coated with at least any of an acid resistant membrane or a sulfuration resistant membrane and a thrombus resistance membrane, respectively.

The first magnet 2 is formed with an insertion recess (recessed portion) 5 for inserting a tip end (a right end shown in FIG. 1) of a flexible guide wire 4 made of a soft material at the center of the back surface 2b of the adsorption surface 2a with a slight play. The tip end of the guide wire 4 is inserted into the insertion recess 5, whereby the guide wire is removably mounted to the recess 5 by filling a temporary bonding adhesive 6 therein. For example, as the temporary bonding adhesive 6, there may be used an adhesive for gradually reducing its adhesion (adhesive force) with an elapse of time or by an acidic liquid or humor in the body and the like.

A cylindrical guide tube 7 is formed of substantially the same structure as a flexible soft drainage tube, for example. When the guide wire 4 is pulled out from the insertion recess 5 of the magnet 2, the tip end surface comes into contact with the back surface 2b of the magnet 2 while the guide wire 4 is inserted therein. Then, the back surface 2b is supported in the axial direction and is inserted into the through hole of the anastomosis site (region) formed as described later, thereby maintaining the formation of the through hole.

The guide wire 4 may be removably mounted to the back surface 2b of the adsorption surface 2a of the first magnet 2 and may be constructed so as to be removably mounted by a fitting mechanism as well as these temporary bonding adhesive 6. In addition, the adsorption surface 2a of the first magnet 2 may be greater than the adsorption surface 3a of the second magnet 3.

Figure 2:
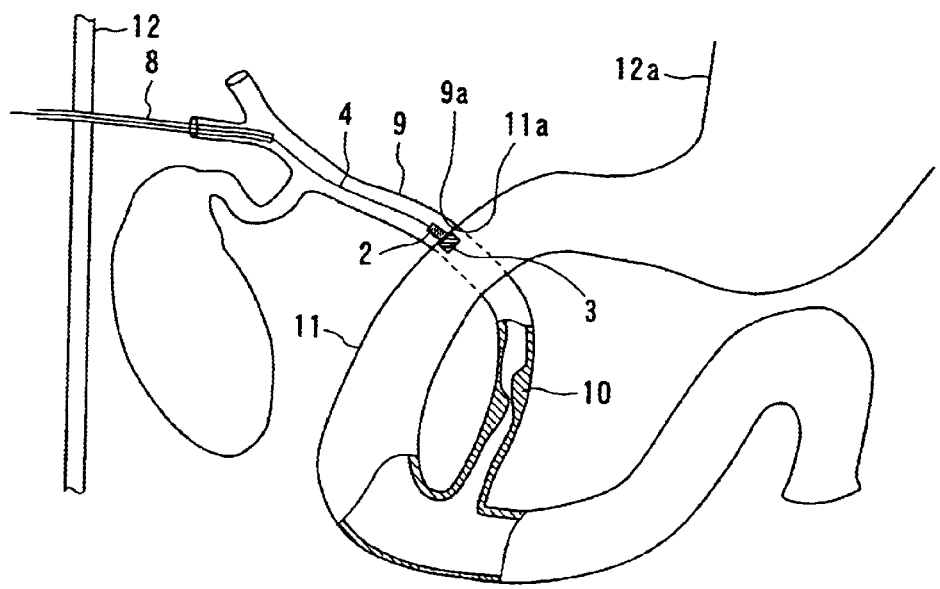
FIG. 2 is a partial longitudinal sectional view showing an organ at the periphery of constriction of a common bile tube for showing an example of a method for forming a bypass for common bile tube constriction by using the organ anastomosing apparatus shown in FIG. 1.

FIG. 2 is a partial cross sectional view showing an organ around a constriction 10 of a bile duct (choledoch) 9 in a case in which, if the constriction 10 occurs with the bile duct 9, a through hole (bypass) that communicates a partial wall 9a of the bile duct 9 on the upstream side of the constriction 10 with the partial wall 11a of the small intestine 11 by using the organ anastomosis apparatus 1 is formed by anastomosis.

In this case, the first magnet 2 is disposed on the upstream side of the constriction 10 of the bile duct 9 and inside the partial wall 9a to be anastomosed, whereas the second magnet 3 is disposed inside the partial wall 11a of the small intestine 11 positioned in the vicinity of the partial wall 9a of the bile duct 9.

Figure 3:
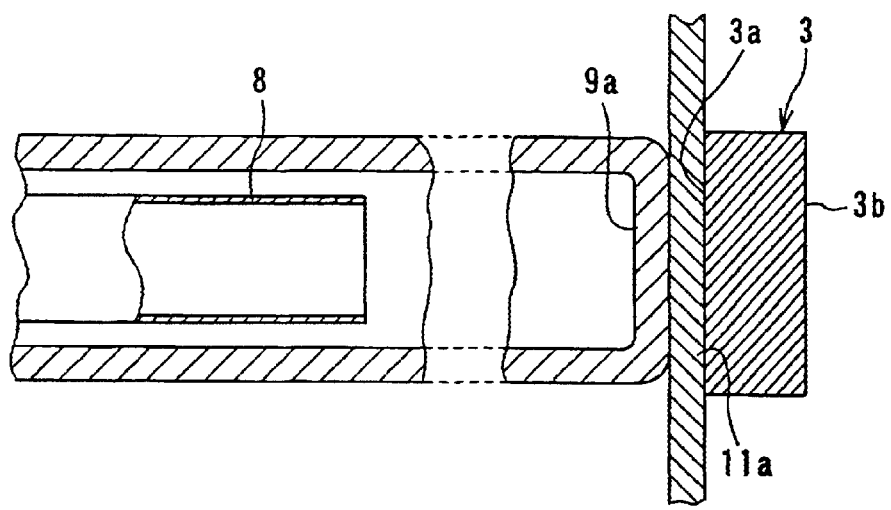
FIG. 3 is an enlarged view of essential parts showing the step of disposing one magnet of the organ anastomosing apparatus shown in FIG. 1 at a predetermined site of the small intestine.

That is, first, a sheath 8 made of a hard cylindrical tube is inserted into the body of a subject such as patient from an endemic and trans-hepatic drainage passage of a hole drilled on an abdominal wall 12 such as flank of the subject's body, is inserted into the bile duct 9 and is disposed in the internal vicinity of the partial wall 9a(refer to FIG. 3). Then, the first magnet 2 is inserted therein from the external opening end of the sheath 8 protruded to the outside of the subject's body. Further, the magnet is inserted into the sheath 8 by holding the guide wire 4 and is pushed and inserted into the body. Thereafter, the magnet is disposed at a predetermined site of the partial wall 9a of the bile duct 9 while an X-ray fluoroscopic screen is observed.

On the other hand, the second magnet 3 is removably held on a pinching forceps made of a non-magnetic object of an endoscope (not shown) and is inserted from the mouth, for example. Further, the magnet is disposed inside the predetermined partial wall 11a of the small intestine 11, and the adsorption surface 3a of the second magnet 3 is opposed to the adsorption surface 2a of the first magnet 2.

However, in the case where the second magnet 3 cannot be disposed at a predetermined site or region by means of the endoscope, the second magnet 3 may be taken into the body of the subject (drunk by a subject such as patient), for example, and is then temporarily moved to the inside of a stomach 12a. Then, the magnet is disposed inside of the predetermined partial wall 11a of the small intestine 11 while the magnet being examined by X-ray fluoroscopy through magnetic guide of an induction magnet (not shown) from the outside of the stomach 12a, whereby the adsorption surface 3a of the second magnet 3 may be opposed to the adsorption surface 2a of the first magnet 2. At this time, the second magnet 3 may be hardly routed because the contraction will occur at the intermediate portion of the intestine. In this case, the magnet is easily routed by routing a predetermined tube to the target intestine for the purpose of induction. Moreover, an operation for contrast can be performed through the tube, and thus, the positioning precision of induction to the predetermined site can be improved.

Figure 4:
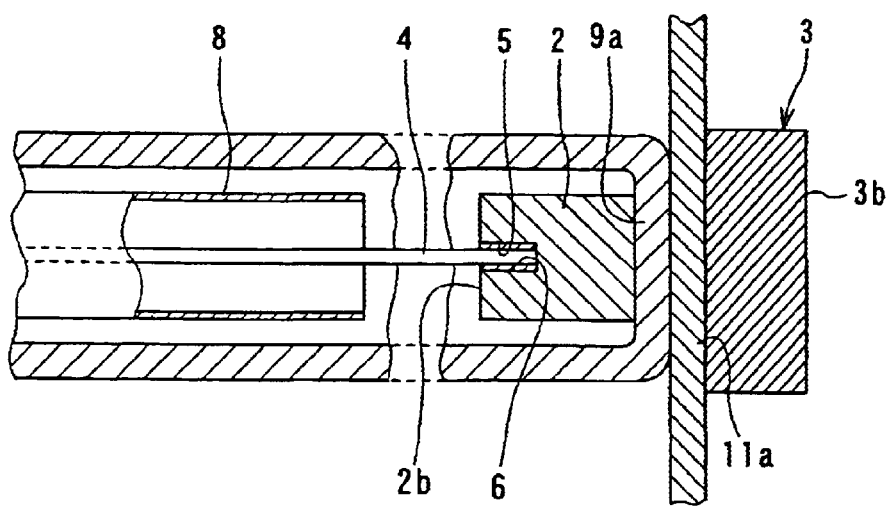
FIG. 4 is an enlarged view of essential parts showing the step of pinching and pressing a partial wall of the common bile tube and a partial wall of the small intestine by a pair of magnets of the organ anastomosing apparatus shown in FIG. 1.

As shown in FIG. 4, when a pair of the adsorption surfaces 2a and 3a of the magnets 2 and 3 are disposed in opposite to each other within a predetermined distance, the adsorption surfaces 2a and 3a are strongly adsorbed to each other by magnetic force through the wall section 11a of the small intestine 11 and the wall section 9a of the common bile duct 9. Thus, both of the wall sections 9a and 11a are strongly pinched and compressed by a pair of the first and second magnets 2 and 3.

Figure 5:
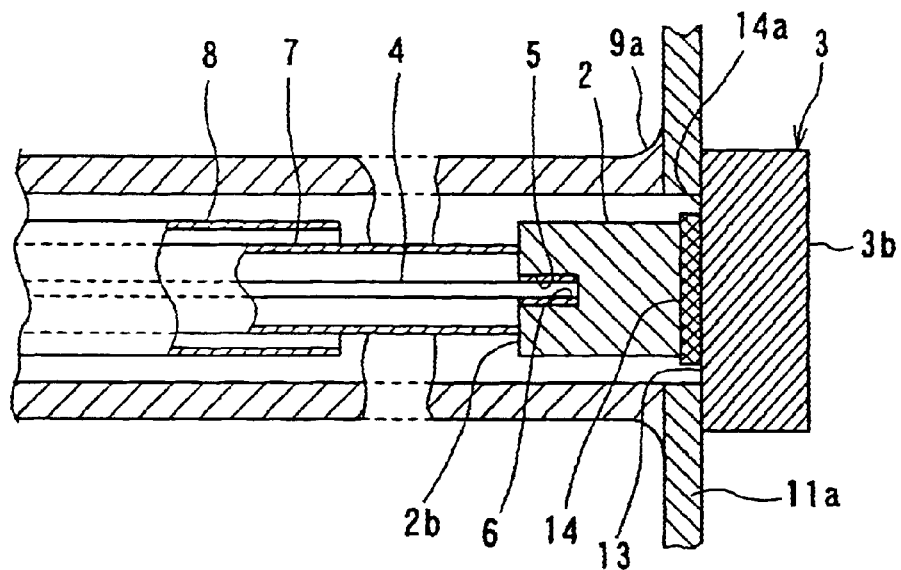
FIG. 5 is an enlarged view of essential parts showing the step of forming anastomosis with a through hole (a bypass) on the partial wall of the common bile tube and the partial wall of the small intestine by using a pair of magnets of the organ anastomosing apparatus shown in FIG. 1.
Figure 6:
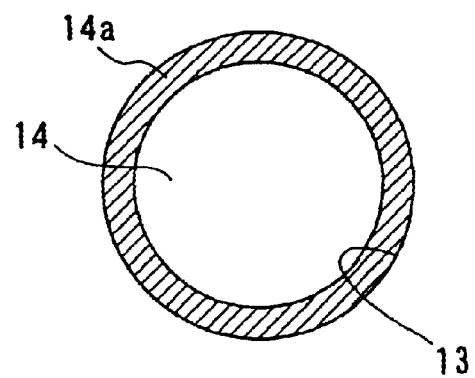
FIG. 6 is a front view showing a through hole of an anastomosis site.

For this reason, as shown in FIG. 5, the peripheral rims (edges) 14a of the pinched and pressed portions 14 of the walls 9a and 11a cause apoptosis, and an anastomosis site is formed. That is, as shown in FIG. 6, the peripheral rims 14a of the pinched and pressed portions cause apoptosis to occur annularly, and a through hole 13 inwardly making communication with the pinched and pressed portions 14 is formed. At the same time, the periphery of the through hole 13 adheres, the anastomosis is formed, and a bypass is thus formed. That is, an upstream side of the constriction 10 of the bile duct 9 can be bypassed partially of the small intestine 11 via the through hole 13, and the bile can be supplied from the common bile duct 9 to the small intestine 11.

After the through hole 13 has been formed, the guide tube 7 is inserted into the outer end of the sheath 8 protruding to the outside of the subject's body and is inserted into the body. Then, while performing an X-ray fluoroscopy, as shown in FIG. 5, the tip end of the guide tube 7 is pressed towards the back surface 2b that is a mount surface of the guide wire 4 of the first magnet 2. In this situation, the guide wire 4 is strongly pulled out towards the outside of the body against the adhesive force of the temporary bonding adhesive 6 and, then, is removed from the first magnet 2.

Figure 7:
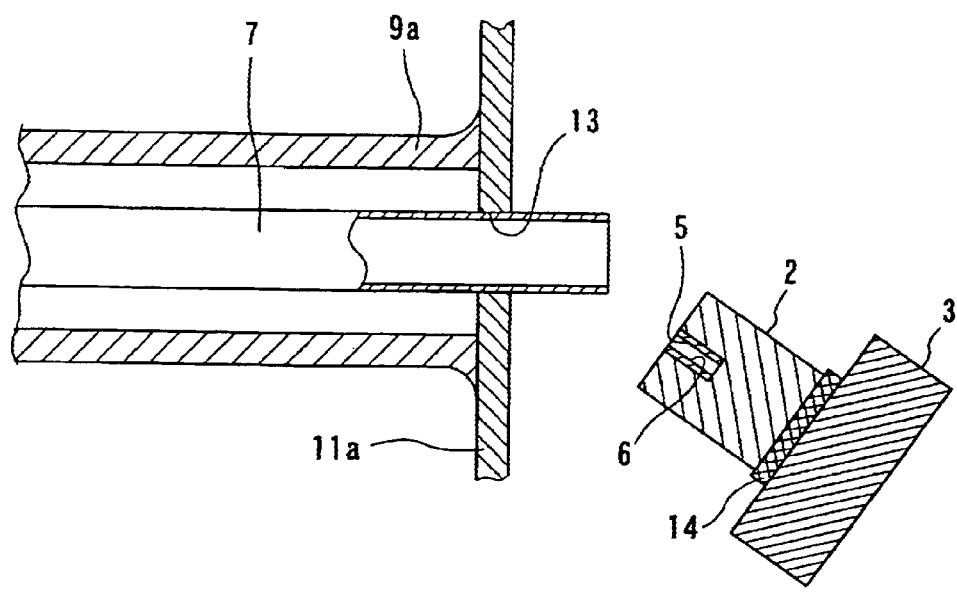
FIG. 7 is an enlarged view of essential parts showing the step of inserting a guide tube of the organ anastomosing apparatus shown in FIG. 1 into the through hole and pushing out a pair of magnets to the small intestine side by means of the guide tube.

Thereafter, while pulling out the entirety of the guide wire 4 to the outside of the body of the subject such as patient through the sheath 8, the tip end of the guide tube 7 is inserted into the through hole 13 in the manner substantially the same as that in the case of the drainage tube as shown in FIG. 7. This insertion state is maintained for a predetermined period of time (for example, about three weeks) until the anastomosis stops. Then, the entirety of the guide tube 7 is pulled out to the outside of the subject's body through the sheath 8. Then, the sheath 8 is removed from the subject's body. For this reason, the through hole 13 can be prevented from closing again due to the anastomotic adhesion, and the through hole 13, i.e., bypass, can be maintained. After the anastomosis has been completed, even if the guide tube 7 is pulled out from the through hole 13, the anastomotic adhesion of the through hole 13 is inhibited.

A pair of magnets 2 and 3 adhering to each other via the pinched and pressed portion 14 are sequentially discharged to the outside of the body together with dejection or the like via the small intestine 11 and the large intestine or the like while maintaining the adsorbed state thereof as it is.

Therefore, according to the organ anastomosing apparatus 1, the first magnet 2 can be easily and surely disposed to the predetermined site or region of the desired organ of the body of the subject by performing suitable operations such as pushing, into the subject's body, the outer end of the guide wire 4 protruding to the outside of the subject's body, pulling it to the outside of the body or turning around the central axis thereof. In addition, after the anastomosis has been formed on the organ walls 9a and 11a, the tip end of the guide tube 7 is inserted into the through hole 13 via the sheath 8 immediately, whereby an occlusion due to the adhesion of the through hole 13 can be stopped efficiently, and the formation of the through hole 13 can be easily maintained. Accordingly, there can be eliminated the complicated steps required in the prior art such as, after the organ walls 9a and 11a have been anastomosed, a drainage tube has to be additionally inserted from a flank into the body independently, for example, the drainage tube is to be further inducted to be inserted to the through hole 13 of the anastomosis site, and its inserted state must be maintained for about three months until the adhesive anastomosis has been stopped.

In addition, both the first and second magnets 2 and 3 are chamfered at their corner portions without forming a sharp cut rim as made in the prior art. Thus, there can be efficiently prevented a danger that the other many organs are damaged by the cut rim until the magnets 2 and 3 have been inducted to be disposed to a predetermined site of a predetermined organ by taking the magnets into the subject's body.

Further, the surfaces of the first and second magnets 2 and 3 are coated with an acid resistant membrane or a sulfuration resistant membrane. Thus, these magnets are prevented or reduced from being oxidized, degenerated, or degraded due to acidic liquid or humor in the body, and the life thereof can thus be extended. In addition, a thrombus resistant membrane is coated on the outer surfaces of the magnets 2 and 3, and thus, the generation of a thrombus due to the magnets in blood can be prevented.

Furthermore, the first and second magnets 2 and 3 are made of a rare earth element, and thus, the magnetic force can be strengthened. Therefore, even if the organ walls 9a and 11a on which anastomosis is to be formed are thick, adsorption between the magnets 2 and 3 can be easily and reliably performed, and the work time can be reduced.

In addition, a pair of magnets 2 and 3 with the strong magnetic forces are adsorbed to each other, and there can be improved the apoptosis of the organ walls 9a and 11a strongly pressed to be pinched by these magnets 2 and 3, the reliability of the formation of the adhesive anastomosis of the through hole 13 making communication with the organ walls 9a and 11a and the adhesive anastomosis around the through hole 13.

Further, the adsorption surface 2a or 3a of one of the paired magnets 2 and 3 is formed to be greater than the adsorption surface 2a or 3a of the other one thereof, and thus, the adsorption between the adsorption surfaces 2a and 3a of the magnets 2 and 3 can be performed more easily and reliably. In addition, the second magnet 3 larger than the first magnet 2 is made larger than the through hole 13, and thus, the magnet can be prevented from moving to the bile duct 9 side through the through hole 13.

Furthermore, in the case where the second magnet 3 is detachably held by the pinching forceps of the endoscope and is disposed at a predetermined site of an organ, the movement of the second magnet 3 in the organ can be observed by the endoscope. Thus, the positioning precision of the second magnet 3 can be improved. Moreover, the pinching forceps of the endoscope is made of a non-magnetic material, and thus, the second magnet 3 is prevented from adhering to the pinching forceps of this endoscope and being hardly removed from the pinching forceps.

Figure 8:
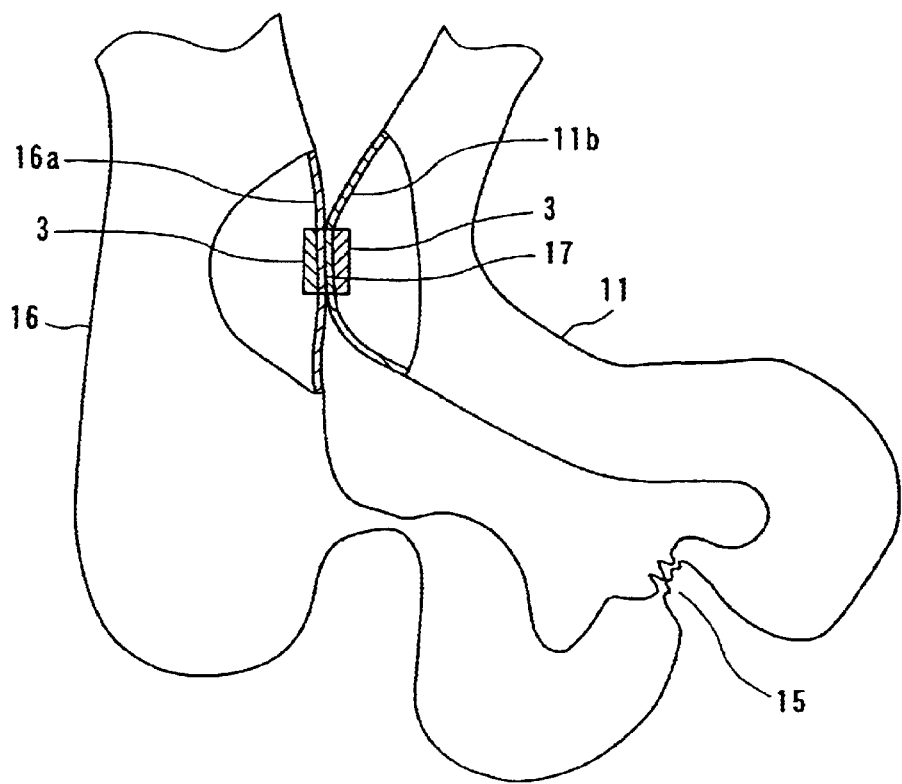
FIG. 8 is a partial longitudinal sectional view of an organ at the periphery of intestinal constriction for showing an example of a method for forming a bypass for intestinal constriction by using the organ anastomosing apparatus shown in FIG. 1.

FIG. 8 is a partial longitudinal sectional view of the organ around the through hole 13 in a case where, if an occlusion 15 (ileus) occurs at the small intestine 11, the through hole 13 (bypass) that communicates the partial wall 11b of the small intestine 11 on the upstream side of the occulsion 15 with a partial wall 16a of a large intestine 16 is formed by anastomosis.

In this case also, there can be formed the through hole 13 (bypass) that communicates the partial wall 11b of the small intestine 11 on the upstream side of the occlusion 15 with the partial wall 16a of the large intestine 16 by using the organ anastomosing apparatus 1 in the same way as with the method mentioned hereinbefore. Now, a case in which the two second magnets 3 are used instead of the first magnet 2 will be described.

Figure 9:
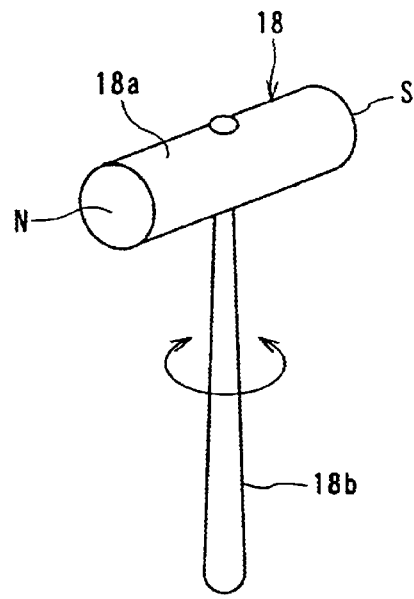
FIG. 9 is an external perspective view showing an induction magnet for inducing the movement of the second magnet of the organ anastomosing apparatus shown in FIG. 1 in the body from the outside of the body.

One magnet 3 disposed inside of the small intestine 11 is induced by the magnetic force of a hammer shaped induction magnet 18 shown in FIG. 9 after the magnet has been taken (drunk) by the subject in the same way as with the aforementioned method and is guided to the partial wall, i.e., predetermined site, 11b in the small intestine 11, or the magnet 3 is pinched by the pinching forceps of the endoscope (not shown) and is disposed so as to oppose the adsorption surface 3a at the predetermined site 11b on the upstream side of the occlusion 15 of the small intestine 11. The other magnet 3 is pinched by the pinching forceps of the endoscope to be inserted from the anal or the like to the large intestine 16. Then, the other magnet 3 is inducted to the predetermined site 16a of the large intestine wall to be disposed in opposite to the one magnet 3. When a pair of these magnets 3, 3 are disposed in opposite to each other, the opposite surfaces of these magnets 3, 3 are properly adjusted from the outside of the body to the N-pole or the S-pole by the induction magnet 18 so as to be adsorbed to each other.

According to this manner, a pair of the magnets 3, 3 are adsorbed while their different poles are opposed to each other, and thus, the partial wall 11b of the small intestine 11 and the partial wall 16a of the large intestine 16 are strongly pinched and compressed from both sides by means of the magnets 3, 3. For this reason, the apoptosis occurs at the peripheral rims of the pressured pinched portions of these walls 11b and 16a, and a through hole 13, which makes inward communication between these walls 11b and 16a, is formed. Further, the periphery of the through hole 13 adheres and is anastomosed to thereby form the the through hole 13. That is, there is formed a bypass which communicates inward between the partial wall 11b on the upstream side of the occlusion 15 of the small intestine 11 and the partial wall 16a of the large intestine 16.

FIG. 9 is a perspective view showing an example of the induction magnet 18. This magnet has a strong magnetic force for inducing the movement of the magnet 3 in the body from the outside thereof. The N-pole and S-pole are provided so as to be orthogonal to a stem 18b at the axial immediate portion of a cylindrical magnet main body 18a, for example, disposed at both ends in the axial direction, and the N-pole and the S-pole are oriented to predetermined directions by turning the stem 18b around the central axis thereof. In addition, by holding the stem 18b, the magnet comes out of the X-ray irradiation area to thereby avoid an exposure from causing.

Figures 10A, 10B:
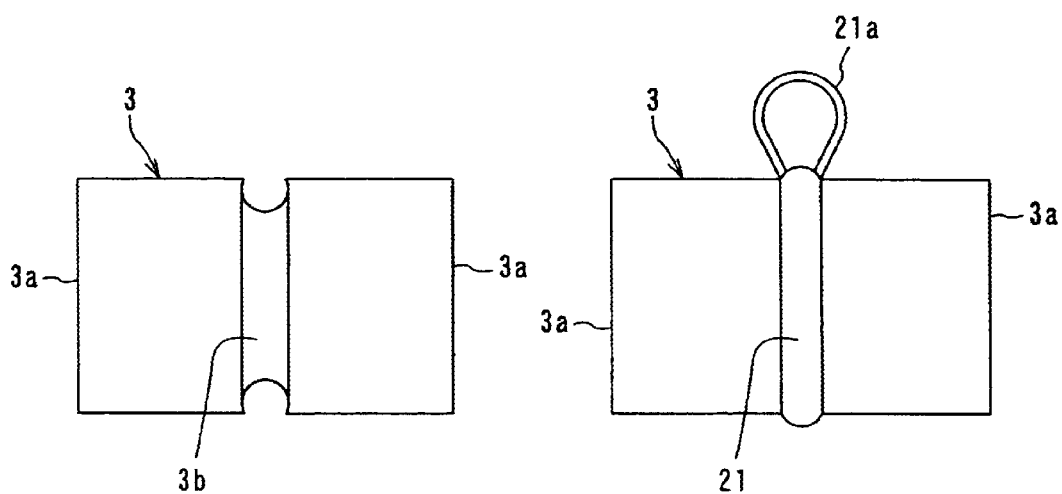
FIG. 10A is a front view of a state in which a string-like recess part is formed in the second magnet shown in FIG. 1
FIG. 10B is a front view of a state in which a string is tightened in its string-like recess.

FIGS. 10A and 10B are front views each showing a modified example of the second magnet 3. The magnet 3 is formed with a fine recess portion (groove) 3b which turns by one turn in the diameter direction of its disc shape. At the recess portion 3b, a string 21 that is a soft holding member made of a non-magnetic material is tightened. Then, a ring shaped small loop 21a is formed at one end (an upper central end shown in FIG. 10) of this string 21, and the loop 21a is pinched by the pinching forceps of the endoscope (not shown). In this manner, the magnet 3 can be easily pinched and be made free from slipping-off while moving the magnet in the body of the subject such as patient. In addition, the string 21 is substantially included in the recess portion 3b and is hardly protruded from the peripheral surface of the magnet 3. This makes it possible to almost prevent the movement of the magnet 3 from being interfered due to the string 21 when the string 21 is caught by a part of an organ while the magnet being moved in the body.

Figure 11:
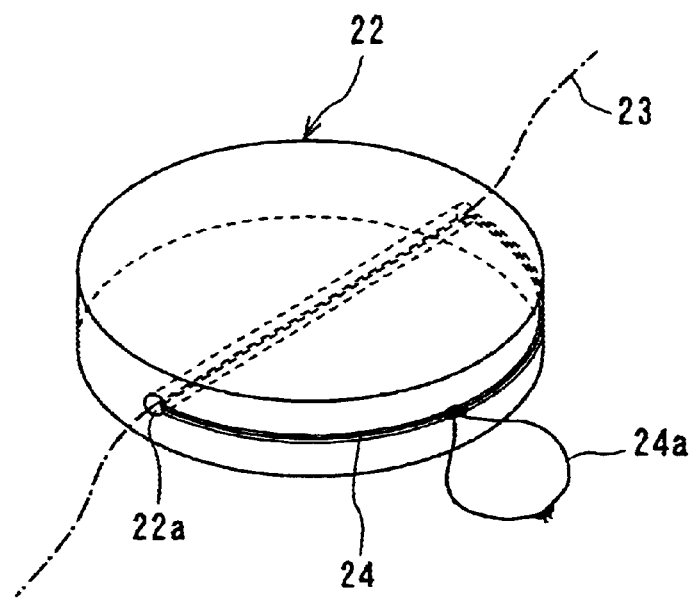
FIG. 11 is an external perspective view showing a modified example of the second magnet shown in FIG. 1.

FIG. 11 is an enlarged perspective view of a magnet 22 showing a modified example of the magnet 3 in the former embodiment. This magnet 22 is formed in a flat and cylindrical (disc) shape, and a through hole 22a is punched on a side peripheral portion thereof so as to penetrate in an almost linear shape in the diameter direction so that an induction wire 23 is to be inserted with play. In addition, a non-magnetic soft string 24 is tightened at the peripheral surface on one side of the magnet 22. The string 24 is inserted into the through hole 22a to be tightened on the peripheral surface on one side of the magnet 22, and a string loop 24a to be pinched by the pinching forceps of the endoscope is formed at this tightened portion. This magnet 22 has its corners chamfered in the same manner as that described with reference to the second magnet 3, and at least one of the acid resistant membrane and the thrombus resistant membrane is coated on the outer surface thereof.

Therefore, in the case where the magnet 22 is disposed at a predetermined site region) in the subject's body, an induction wire 23 is first inserted into the subject's body, and then, the tip end thereof is disposed in the vicinity of a predetermined site in the body.

Next, while inserting the through hole 22a of the magnet 22 into an end portion extending to the outside of the induction wire 22, the string loop 24a of the magnet 22 is pinched by the pinching forceps of the endoscope, is moved into the body along the inducing wire 23 and is inducted to the predetermined site.

Therefore, according to this magnet 22, the magnet 22 is inducted to the predetermined site in the body along the induction wire 23 so that its induction precision can be improved. In the illustrative embodiment, although there is shown the case in which the anastomosing apparatus 1 of the present invention is used to cause the anastomosis between the bile duct 9 and the small intestine 11 and between the small intestine 11 and the large intestine 16, the present invention is not limited to this embodiment, and the present invention may be used for the anastomosis between digestive systems, blood vessels, ureter, bladders, skins, bones and the like or anastomosis with organs in the vicinity thereof.

Figure 12:
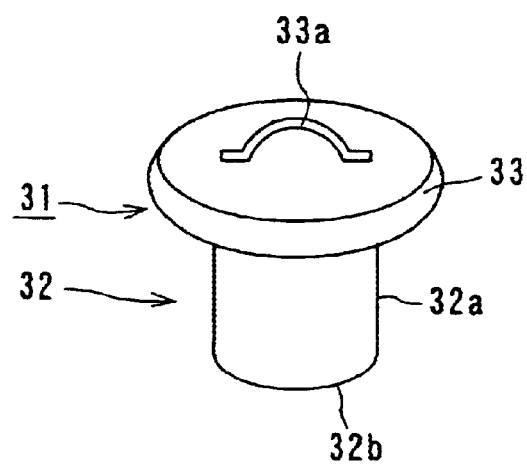
FIG. 12 is a perspective view showing one of a pair of fourth magnets of the organ anastomosing apparatus according to a second embodiment of the present invention.

FIG. 12 is a perspective view showing one of a pair of fourth magnets 32, 32 of an organ anastomosing apparatus 31 according to a second embodiment of the present invention. This organ anastomosing apparatus 31 has a pair of fourth magnets 32, 32. Each of these magnets 32 has a cylindrical or rectangular magnet main body 32a of a desired size and formed with chamfered corners at one of the adsorption surfaces 32b which are formed at end portions so as to be magnetically adsorbed to each other with their different magnetic poles.

Each magnet main body 32a is made of a rare earth element, for example, and at least either one of the acid resistant membrane or sulfuration resistant membrane and the thrombus resistant membrane is coated on the outer surface thereof.

Figure 13:
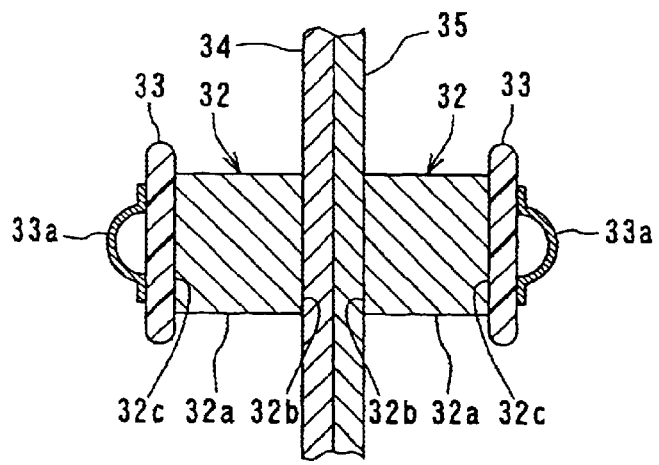
FIG. 13 is a longitudinal sectional view of essential parts showing a state in which a pair of the magnets shown in FIG. 12 are adsorbed to each other via a pair of desired organ walls.

In addition, as shown in FIG. 12 and FIG. 13, a disc shaped large-diameter end 33 which is larger than the adsorption surface 32b and an opening diameter of the adsorption surface 32b is coaxially integrated with or integrally mounted on each of the other end surfaces 32c on the axial opposite side of the adsorption surface 32b of each magnet main body 32a.

Although the large diameter end 33 is formed of plastics or the like material, for example, in a disc shape, the end 33 may be formed of a raw material such as plastics fused in the subject's body after an elapse of a desired period of time (for example, a desired period of about three months or more) in a disc shape having corners being chamfered.

In addition, a protrusive, semi-arc shaped grip 33a is formed integrally at substantially the central portion of the axial outer end surface of the large diameter end 33, so that the grip 33a is pinched by the pinching forceps of the endoscope (not shown).

FIG. 13 is a longitudinal sectional view showing a state in which a pair of the fourth magnets 32, 32 thus constructed are disposed in opposite to each other at the predetermined sites of a pair of walls 34, 35 of a desired organ at which a bypass (through hole 13) is to be formed.

That is, one of a pair of the fourth magnets 32, 32 is taken (drunk) from the mouse of the subject's body, and while observing the position of the magnet 32 through X-ray irradiation fluoroscopy or the like, the magnet 32 is moved from the outside of the subject's body to a predetermined site of the desired organ wall 34 or 35 by means of an induction magnet 18 shown in FIG. 9.

On the other hand, with respect to the other magnet 32, the grip 33a thereof is pinched by the pinching forceps of the endoscope (not shown), for example. Then, the magnet is disposed at the predetermined site of the desired organ wall 34 or 35 of the subject's body and is disposed in opposite to one magnet 32 via both the walls 34 and 35.

Figure 14:
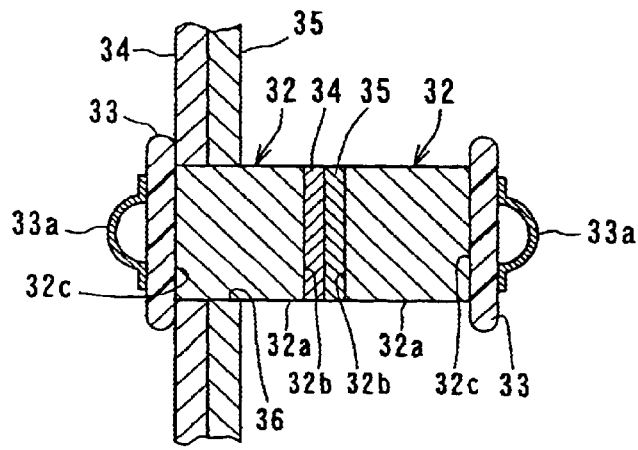
FIG. 14 is a longitudinal sectional view showing a state in which a pair of fourth magnets shown in FIG. 13 are inhibited from slipping off from a through hole after the through hole has been punched on a pair of desired organ walls.

Then, both the adsorption surfaces 32b, 32b of a pair of the magnets 32, 32 are adsorbed substantially coaxially by the magnetic adsorption force through both the walls 34 and 35, which are strongly pinched and compressed by a pair of the magnets 32, 32. This compression causes apoptosis to occur at the compressed portion or peripheral edge or rim of the walls 34 and 35 after an elapse of period of time. As shown in FIG. 14, a through hole 36 having a diameter substantially the same as that of the magnets 32, 32 is then formed at both the walls 34 and 35, the walls 34 and 35 at the periphery rim of the through hole 36 adhere, the anastomosis is formed, and the bypass is formed so as to establish the communication between the desired organs.

Figure 16:
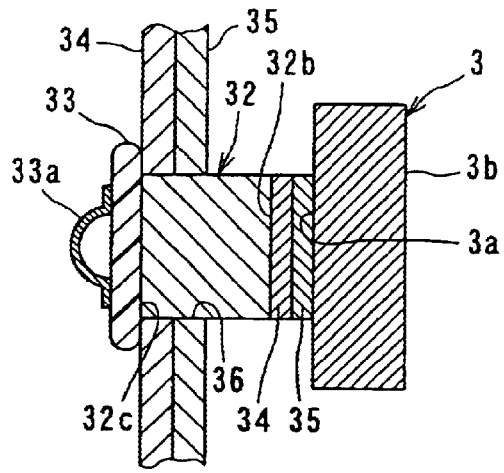
FIG. 16 is a longitudinal sectional view of essential parts showing a state in which the second and forth magnets shown in FIG. 15 are inhibited from slipping off from a through hole after the through hole has been punched on a pair of desired organ walls.

However, as shown in FIG. 16, the large diameter ends 33 and 33 of a pair of magnets 32, 32 adsorbed to each other have a diameter larger than the diameter of the though hole 36. Thus, even if the through hole 36 is opened, both the large diameter ends 33 of the magnets 32, 32 are engaged and fitted in the through hole 36, whereby a pair of the magnets 32 can be prevented from slipping off from the through hole 36 in the axial direction.

For this reason, after a desired period of time (for example, three months or more) has elapsed while maintaining the state that a pair of the magnets 32, 32 are inserted into the through hole 36, the anastomosis action substantially stops at the anastomosis site of the peripheral rim of the through hole 36.

Then, the grip 33a is pinched at one of the paired magnets 32, 32 by the pinching forceps of the endoscope or the like, and a pulling force is applied towards one side of the walls 34 and 35. Accordingly, one of the large diameter ends 33 of the paired magnets 32, 32 abuts against an opening end of the through hole 36, and the peripheral rim of the through hole 36 is elastically deformed. Then, the large diameter end 33 passes through the through hole 36, is pulled out to an organ on one side of the walls 34 and 35, and then, is discharged to the outside of the subject's body together with the dejection or the like.

Therefore, after the through hole (bypass) 36 is communicated to the pair of these walls 34 and 35, the paired magnets 32, 32 are temporarily left in this through hole 36 without the magnets being pulled off from the though hole 36 immediately. Thus, the through hole 36 is prevented from being closed by the anastomosis, and the formation of the through hole 36 can be maintained.

Figure 15:
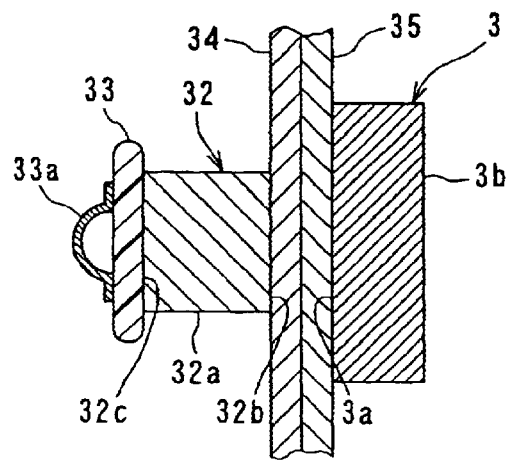
FIG. 15 is a longitudinal sectional view of essential parts showing a state in which the fourth magnet shown in FIG. 12 and the large second magnet shown in FIG. 1 or the like are adsorbed to each other via a pair of desired organ walls.

FIG. 15 is a longitudinal sectional view showing a state in which the magnets 32, 32 are disposed in opposite each other at their predetermined sites via a pair of walls 34 and 35 in order to form the bypass, i.e., the through hole 36 to a pair of the walls 34 and 35 of a desired organ by one of the paired fourth magnets 32 and 32 shown in FIG. 12 and the large second magnet 3 shown in FIG. 1 or the like.

That is, the second magnet 3 and the fourth magnet 32 are adsorbed to each other through a pair of the walls 34 and 35 by the magnetic adsorption force, and these walls 34 and 35 are strongly pressed to be pinched and are compressed. Thus, the compression causes the apoptosis to occur at a non-compressed portion or peripheral rim of the walls 34 and 35 after a desired period of time has elapsed. As shown in FIG. 16, the through hole 36 having a shape substantially the same as that of a small third magnet 32 is opened so as to communicate with the walls 34 and 35.

The through hole 36 is smaller than each of the large diameter ends 33 of the large second magnet 3 and the small fourth magnet 32. This prevents the mutually absorbed second and fourth magnets 3 and 32 from slipping off from the through hole 36 and the through hole 36 from being closed due to the anastomotic adhesion, and the formation of the through hole 36 can be maintained.

After the formation of the through hole 36 has been maintained, the grip 33a of the third magnet 32 is pinched by the pinching forceps of the endoscope (not shown), while the X-ray irradiation fluoroscopy being performed and is pushed to the second magnet 3 side, for example. Alternatively, the large second magnet 3 is pinched by the pinching forceps of the endoscope and is introduced into the second magnet side.

Accordingly, the large diameter end 33 of the fourth magnet 32 abuts against an opening end of the hole 36, is elastically deformed together with the anastomosis site of the peripheral rim of the through hole 36, and is forcibly inserted into the through hole 36. Further, the large diameter end 32 of the forth magnet 32 passes through the inside of the through hole 36 and is pulled out to the organ on the large second magnet 3 side. Then, a pair of the magnets 32 and 32 are discharged to the outside of the body while the magnets being adsorbed to each other.

Therefore, the magnets 32 and 32 are left while being inserted in the through hole 36 after the through hole 36 has been formed on a pair of the walls 34 and 35. This prevents the through hole 36 from being closed by the anastomosis and the formation of the through hole 36 can be maintained.

Figure 17:
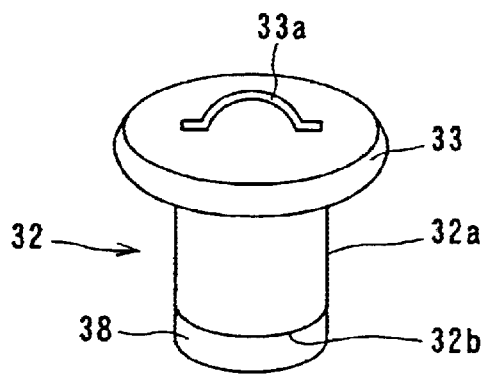
FIG. 17 is a perspective view showing a modified example of the fourth magnet shown in FIG. 12.
Figure 18:
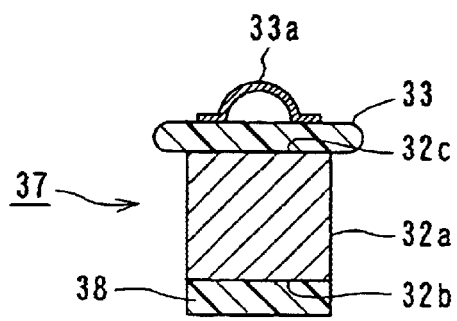
FIG. 18 is a longitudinal sectional view of the fourth magnet shown in FIG. 17.

FIG. 17 is a perspective view showing a fifth magnet 37 according to a modified example of each of the above magnets 32, and FIG. 18 is a longitudinal sectional view thereof. This fourth magnet 37 is characterized in that a spacer 38 formed of a non-magnetic material such as plastics having the shape substantially the same as the cylindrical shape of the adsorption surface 32b or a cylindrical shape closed at both ends in the axial direction is coaxially fixed to an adsorption surface 32b of the third magnet 32. The other structure is the same as that of the above fourth magnet 32. In FIG. 17, like elements are designated by like reference numerals or numbers.

The axial length of the spacer 38 is properly selected, for controlling the mutual magnetic adsorption force between a pair of fifth magnets 37, 37, so as to have a thickness of an organ at which the through hole (bypass) 36 is to be formed or a thickness of the wall 34 or 35, or an optimal value according to a variety of purposes of shunting operation. Thus, plural types of the fifth magnets 37 having the spacers 38 of different axial lengths are preliminarily prepared.

Therefore, in the case where the through hole 36 is formed on the paired walls 34 and 35 of a desired organ by means of the paired magnets 37, 37, the paired walls 34 and 35 can be pressed to be pinched by an adequate magnetic suction force corresponding to the thickness of the organ or the wall 34 or 35 or the like. On the other hand, there is no need for controlling the magnetic adsorption force of the magnet main bodies 32a, 32a themselves, and thus, the improvement in efficiency can be achieved.

When the large diameter ends 33 of the fourth and fifth magnets 32 and 37 are left in the subject's body for a predetermined period of time, these magnets may be composed of a raw material such as plastics fused by the humor of the body or the like. Accordingly, in the case where a pair of the mutually adsorbed magnets 37, 37 left in the temporarily punched through hole 36 do not provide such a danger as that the through hole 36 is closed at a time when the anastomosis action of the through hole 36 stops, and after each of the large diameter ends 33 of the magnets 32 and 37 is fused to be reduced to be smaller than the opening diameter of the through hole 36, a pair of these magnets 37, 37 pass through the inside of the through hole 36 by the organ activity, move into the organ of one side of the walls 34 and 35, and then, are discharged outside of the subject's body together with the dejection or the like.

Therefore, in this case, the through hole 36 is punched, and a pair of the fifth magnets 37, 37 left therein are pinched by the pinching forceps of the endoscope or the like, whereby a work for discharging the magnets to the outside of the body can be eliminated.

Figure 19:
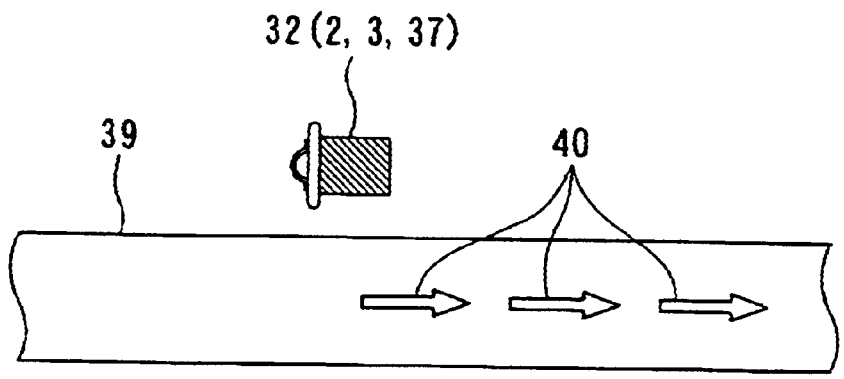
FIG. 19 is a front view of a partial cutout showing a part of an ileus tube for guiding the movement of each of the magnets shown in FIG. 1 to FIG. 18.

FIG. 19 is a front view, partially cutout, showing an ileus tube 39 that is a drainage tube for guiding movement of each of the above magnets 2, 3, 32 and 37. The ileus tube 39 is composed of a tube having the inner diameter smaller than each of the magnets 2, 3, 32 and 37, the tube being made of flexible plastics or the like, for example, and being inserted into long intestines or the like in the subject's body.

In the ileus tube 39, a plurality of arrows 40, which are examples of signs indicating the movement direction of each of the magnets 2, 3, 32 and 37, are marked on its outer surface with a radiation (X-ray) transmission-free material such as lead (Pb), barium (Ba), platinum (Pt) or the like.

Figure 20:
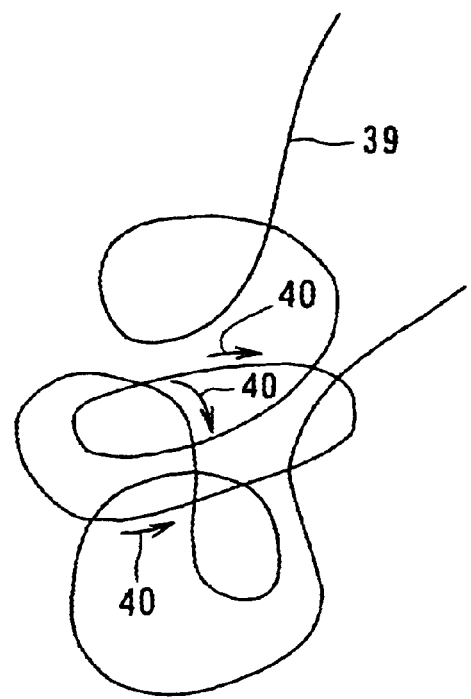
FIG. 20 is a schematic view of X-ray fluoroscopy when the ileus tube shown in FIG. 19 is inserted into the intestine.

For this reason, as shown in FIG. 20, in the case where the ileus tube 39 is inserted from the mouse or the like, for example, into the subject's body, is further inserted into the long intestine and is subjected to the X-ray fluoroscopy from one surface, this ileus tube 39 is complicated, which sometimes makes it difficult to identify the movement direction of each of the magnets 2, 3, 32 and 37. In the case of the X-ray fluoroscopy, the arrow 40 indicating the insertion direction of each of the magnets 2, 3, 32 and 37 is expressed by the X-ray transmission free material on the outer surface of the ileus tube 39, and the arrow 40 can be visually checked.

Therefore, any of the magnets 2, 3, 32 and 37 inserted into the subject's body together with the ileus tube 39 is inducted in the direction indicated by the arrow 40 by means of the induction magnet 18 from the outside of the subject's body along the outer face of the ileus tube 39. In this manner, the magnet can be moved efficiently and smoothly without any problem.

A substance for promoting the anastomosis of membrane growth factors in blood vessels or the like may adhere, in advance, to any of the magnets 2, 3, 32 and 37 or the spacer 38. Accordingly, after each of the through holes 13 and 36 (bypasses) has been punched, the opening peripheral rims of the through holes 13 and 36 come into contact with the membrane growth factors in blood vessels adhering in advance to each of these magnets 2, 3, 32 and 37 or the spacer 38. For this reason, the speediness of the anastomosis can be improved.

What is claimed is:

1. An organ anastomosing apparatus comprising:
    a pair of magnets, including a first magnet and a second magnet, being disposed to predetermined sites of organs of a subject to be anastomosed to each other to be opposed through wall portions of the respective organs, the pair of magnets including a plurality of adsorption surfaces on each of the first and second magnets, thereby enabling adsorption of the first and second magnets to each other to form an anastomosis site having a through hole for making communication between the organ walls;
    a flexible guide wire detachably mounted to at least the first magnet; and
    a guide tube inserted into a body of the subject with said guide wire being inserted therein, said guide tube coming into contact with a guide wire mount surface of said first magnet to support the first magnet, said guide tube being configured to be inserted into the through hole of the anastomosis site to maintain formation of the through hole,
    wherein the plurality of adsorption surfaces on each of the first and second magnets includes a first surface having a first pole and a second surface having a second pole that is different from the first pole.

2. An organ anastomosing apparatus according to claim 1, further comprising a cylindrical sheath inserted into the body of the subject from an outside thereof so as to insert the first magnet to which the guide wire is mounted to guide the first magnet in a vicinity of the predetermined sites of organs.

3. An organ anastomosing apparatus according to claim 1, wherein said first magnet has an adsorption surface larger in dimension than that of the second magnet.

4. An organ anastomosing apparatus according to claim 1, wherein said paired magnets are formed in substantially a same size.

5. An organ anastomosing apparatus according to claim 1, wherein a surface of said first magnet is coated with at least one of an acid resistant membrane and thrombus resistant membrane.

6. An organ anastomosing apparatus according to claim 1, wherein said first magnet is made of a rare earth element.

7. An organ anastomosing apparatus according to claim 1, wherein said second magnet is taken into the subject's body and then guided from an outside thereof by means of an induction magnet to a predetermined site of the organ of the subject.

8. An organ anastomosing apparatus according to claim 7, wherein said induction magnet has an N-pole and an S-pole opposite to each other and an axial intermediate portion to which a stem is provided to extend in a direction perpendicular to the axial intermediate portion.

9. An organ anastomosing apparatus according to claim 1, wherein said second magnet is removably pinched by pinching means of an endoscope to be disposed at the predetermined site of the organ of the subject's body.

10. An organ anastomosing apparatus according to claim 9, wherein the inching means of the endoscope is made of a non-magnetic material.

11. An organ anastomosing apparatus according to claim 9, wherein said second magnet is provided with a flexible non-magnetic holding member to be pinched by the pinching means of the endoscope.

12. An organ anastomosing apparatus according to claim 1, wherein said organ is any one of digestive system, blood vessel, ureter, bladder, skin, and bone.

13. An organ anastomosing method comprising the steps of:
    preparing a pair of magnets, including a first and a second magnet and having a plurality of adsorption surfaces on each of the first and second magnets, to at least one of which a flexible guide wire is detachably mounted, guide tube to be disposed to come into contact with a guide wire mount surface of the first magnet and a cylindrical sheath to guide the guide wire;
    disposing the second magnet at a predetermined site of one of organ walls of a subject to be anastomosed to each other;
    inserting the cylindrical sheath from an outside of a subject into a body of the subject;
    inserting the first magnet for detachably mounting the flexible guide wire into the sheath and inserting the magnet into the other one of the organ walls to dispose the magnet at a predetermined site, the organ being adsorbed by said first magnet to said second magnet, thereby pinching a portion of the organ wall;
    forming a through hole to establish a communication between the organ walls by pinching the organ walls and forming an anastomosis around the through hole;
    removing the guide wire from the first magnet by pulling the guide wire towards the outside of a body of the subject when said guide tube is inserted into said sheath to support a tip end of the guide tube in contact with a guide wire mount surface of said first magnet;
    leaving the guide tube for a predetermined period of time while inserting the guide tube into the through hole of the anastomosis site; and
    pulling out the guide tube from the anastomosis site and the subject's body after an elapse of the predetermined period of time, wherein the plurality of adsorption surfaces on each of the first and second magnets includes a first surface having a first pole and a second surface having a second pole that is different from the first pole.

14. An organ anastomosing method according to claim 13, wherein the second magnet is induced from the outside of the body of the subject and guided to the predetermined site of the organ.

15. An organ anastomosing method according to claim 13, wherein the second magnet is detachably pinched by pinching means of an endoscope and disposed at the predetermined site of the organ.

16. An organ anastomosing method according to claim 13, wherein the first magnet has an adsorption surface larger in size than that of the second magnet.

17. An organ anastomosing apparatus, wherein a pair of magnets including a first magnet and a second magnet and having a plurality of adsorption surfaces on each side of the first and second magnets, configured to be disposed opposite to each other at a predetermined site of organ walls of a subject to be anastomosed each other via respective organ walls, the first and second magnets being configured to be adsorbed to each other to form an anastomosis site having a through hole making communication between the organ walls, and wherein a large diameter end larger than respective ends of the through hole is provided at each end of an opposite side of both adsorption surfaces of the first and the second magnets, and wherein the plurality of adsorption surfaces on each of the first and second magnets includes a first surface having a first pole and a second surface having a second pole that is different from the first pole.

18. An organ anastomosing apparatus according to claim 17, wherein each of the first and the second magnets has a grip provided on an outer end surface of the large diameter end.

19. An organ anastomosing apparatus according to claim 17, wherein the large diameter end of each of the first and the second magnets is made of a row material fusible in the subject's body after an elapse of a predetermined period of time.

20. An organ anastomosing apparatus according to claim 17, wherein at least one of the first and the second magnets is mounted with a spacer made of a non-magnetic material at an end opposite the large diameter end.

21. An organ anastomosing apparatus according to claim 17, further comprising a drainage tube configured to be inserted into the subject's body, said drainage tube being configured to guide movement of the first or the second magnet along an outer surface thereof and a sign indicative of a moving direction of said first or said second magnet is marked with a radiation transmission-free material.

22. The organ anastomosing apparatus according to claim 1, wherein a substance promoting anastomosis of membrane growth factors is adhered to at least one of the first and second magnets.

23. The organ anastomosing method according to claim 13, wherein a substance promoting anastomosis of membrane growth factors is adhered to at least one of the first and second magnets.

24. The organ anastomosing apparatus according to claim 17, wherein a substance promoting anastomosis of membrane growth factors is adhered to at least one of the first and second magnets.

* * * * *